United States Patent [19]

Fischer

[11] Patent Number: 5,290,259
[45] Date of Patent: Mar. 1, 1994

[54] DOUBLE SYRINGE DELIVERY SYSTEM

[75] Inventor: Dan E. Fischer, Sandy, Utah

[73] Assignee: Ultradent Products, Inc., South Jordan, Utah

[21] Appl. No.: 20,326

[22] Filed: Feb. 18, 1993

[51] Int. Cl.⁵ .............................................. A61M 5/00
[52] U.S. Cl. ..................... 604/218; 604/191; 222/137
[58] Field of Search .............. 604/191, 187, 218, 82, 604/181, 227; 222/134–137

[56] References Cited

U.S. PATENT DOCUMENTS

| | | | |
|---|---|---|---|
| 3,467,096 | 9/1969 | Horn. | |
| 3,552,394 | 1/1971 | Horn. | |
| 3,746,216 | 7/1973 | Frederick | 222/137 |
| 3,828,980 | 8/1974 | Creighton et al. | 222/137 |
| 4,040,420 | 8/1977 | Speer. | |
| 4,109,653 | 8/1978 | Kozam et al. | |
| 4,121,739 | 10/1978 | Devaney et al. | 222/137 |
| 4,260,077 | 4/1981 | Schroeder | 222/137 |
| 4,359,049 | 11/1982 | Redl et al. . | |
| 4,367,737 | 1/1983 | Kozam et al. . | |
| 4,381,778 | 5/1983 | Kozam et al. | 604/191 |
| 4,609,371 | 9/1986 | Pizzino | 604/191 |
| 4,610,666 | 9/1986 | Pizzino | 604/191 |
| 4,631,055 | 12/1986 | Redl et al. | 604/82 |
| 4,735,616 | 4/1988 | Eibl et al. | 604/191 |
| 4,872,866 | 10/1989 | Davis | 604/227 |
| 4,874,368 | 10/1989 | Miller et al. | 604/82 |
| 4,979,942 | 12/1990 | Wolf et al. | 604/83 |
| 5,049,135 | 9/1991 | Davis | 604/181 |
| 5,116,315 | 5/1992 | Capozzi et al. | 604/82 |

Primary Examiner—John D. Yasko
Attorney, Agent, or Firm—Workman Nydegger Jensen

[57] ABSTRACT

A double syringe delivery system is disclosed for holding a pair of syringes in a manner so as to accommodate the simultaneous activation of the plunger of each syringe in order to effect simultaneous delivery of the contents of each syringe. The double syringe delivery system includes an elongated support member that is placed between the barrel of each syringe. The elongated support member has resilient, C-shaped clamps on opposite sides of the support member. The clamps are used for holding the syringe barrels of both syringes so that the syringe barrels will be held together in a parallel manner. Further, elongated support member and clamps hold the syringe barrels in a fashion that is slightly longitudinally offset from one another to permit the two syringe barrels to be held together as closely as possible. An interconnecting bridge member connects the two syringe plungers so that they can also be simultaneously activated even though they are also slightly longitudinally offset from one another.

20 Claims, 5 Drawing Sheets

DOUBLE SYRINGE DELIVERY SYSTEM

BACKGROUND

1. Field of the Invention

The invention is in the field of systems utilized to measure out and mix two or more fluids, including freely flowing fluids and viscous fluids, by delivering them simultaneously to a single location. More particularly, the invention's field concerns systems for measuring and mixing by simultaneously dispensing freely flowing and viscous fluids from multiple interconnected syringes.

2. Prior State of the Art

There are many types of procedures that require the mixing of two or more substances before the mixed compound can be used. For example, in the field of dentistry a common practice in the dental arts is to measure separate substances, drop-wise, into a well or mixing dish and to then mix the separate substances together using an applicator brush, which in turn is then used to apply the mixed compound to teeth surfaces. More recently, more advanced mixing and delivery applicator syringes have been devised that permit mixing to occur within the same syringe used for delivery. As will be appreciated, in dentistry, it is often necessary to mix relatively small amounts because of the small surface areas that are to be worked upon. Furthermore, the materials which are mixed are often expensive, and rather than mix large quantities, relatively small quantities are mixed repeatedly so as to not waste undue amounts of the materials in question.

In such types of applications, not only is it important to be able to carry out the mixing procedure quickly and efficiently, but in order to do so, it is also important to be able to quickly, efficiently and accurately deliver the proper amounts of the two compounds that are to be mixed together. Such compounds are often delivered from syringes or other dispensers from which the compounds may be delivered in a drop-wise fashion. However, delivery from separate syringes or other drop-type dispensers can often unduly complicate the mixing process and can sometimes lead to inaccuracy or wasted time. For example, when delivering different compounds into a common mixing receptacle from different dispensers, if one of the dispensers is misplaced, additional time may be necessary to find and locate it. In the meantime, one must keep track of the amount of compound that has already been delivered from one dispenser, so that when the other dispenser is found, the appropriate ratio or amounts of the compounds will be mixed.

Another problem that occurs when using separate dispensers for delivery of compounds that are to be mixed, is the additional time that is necessary in order to deliver the compounds to the mixing receptacle. Each compound must be separately measured and dispensed thus, in effect, doubling the amount of time that is required to accurately deliver the two compounds for mixing. Accordingly, there is a need in the art for delivery systems which are more efficient, which are less time consuming to use, and which are more accurate and less susceptible to error in connection with the delivery of two compounds that require mixing.

BRIEF SUMMARY AND PRINCIPAL OBJECTS OF THE INVENTION

The system of the present invention seeks to resolve the above and other problems which have been experienced in the art. More particularly, the present invention provides an improved double syringe system which seeks to overcome many of the problems and disadvantages experienced in the prior state of the art, as evidenced by the following objects and advantages realized by this invention. While the double syringe delivery system of the present invention has been developed specifically for use in the dental arts, it is to be understood that the present invention will find a wide range of application in various types of arts in addition to the dental arts, although the invention as illustrated and described herein has been specifically developed for use in that art.

One primary object of the present invention is to provide a double syringe delivery system wherein two standard syringes can be clipped together so that the two syringes are held together as closely as possible so that they can be simultaneously actuated to eject equal amounts of the fluids contained in each syringe.

A further important object of the present invention is to provide a double syringe delivery system wherein two standard syringes are held together as closely as possible and are therefore longitudinally slightly offset from one another but are nonetheless locked together in such a way that the syringe plungers are also locked in the same longitudinally offset relationship so that the syringe plungers can be simultaneously activated to expel equal amounts of the fluids contained in both syringes.

Still a further object of the present invention is to provide a double syringe delivery system wherein the syringe plungers of each syringe are locked together and are also prevented from longitudinal movement relative to one another when they are joined together.

Still a further object of the present invention is to provide a double syringe delivery system wherein the syringe barrels of each syringe, when locked together, are still largely visible to permit visual inspection of the contents of each syringe barrel.

Yet a further object of the present invention is to provide a double syringe delivery system wherein standard delivery tips having long, flexible delivery tubes are joined together at the distal ends thereof such that the flexible tubes can be flexibly bent or angled in any direction to permit simultaneous ejection out of the distal ends of the flexible tubes of equal amounts of the fluids expelled from the syringes.

These and other objects and features of the present invention will become more fully apparent from the following description and appended claims taken in conjunction with the accompanying drawings. Additional objects and advantages of the present invention may be learned by the practice of the invention.

Briefly described, in the presently preferred embodiment of the double syringe delivery system of the present invention, the delivery system is comprised of an elongated support member that is interposed between the syringe barrels of two standard syringes. Elongated support member has four resilient C-shaped clamps which are spaced from one another on opposite ends of the support member. Two of the clamps on each side of the support member can be snapped onto a syringe barrel of one of the syringes. In this fashion, the two syringes will be held together as closely as possible in a parallel manner. The double syringe delivery system also comprises an interconnecting bridge member that attaches to the end of the syringe plungers so as to join the syringe plungers together to permit simultaneous actuation of the syringe plungers.

In a further aspect of the present invention, the double syringe system can also optionally include a retainer that is used to join the distal ends of the delivery tips attached to each syringe so as to permit simultaneous drop-wise or other dispensing of fluids expelled from the two syringes as the syringe plungers are simultaneously actuated.

BRIEF DESCRIPTION OF THE DRAWINGS

In order to more fully understand the manner in which the above-recited and other objects and advantages of the invention are obtained, a more particular description of the invention will be rendered by reference to a specific embodiment and the presently understood best mode thereof which is illustrated in the appended drawings. Understanding that these drawings only depict the presently preferred embodiment of the invention and are not therefore to be considered as limiting of its scope, the invention will be described and explained with additional specificity and detail through the use of the accompanying drawings in which.

DETAILED DESCRIPTION OF THE ILLUSTRATED EMBODIMENTS

Figure 1:
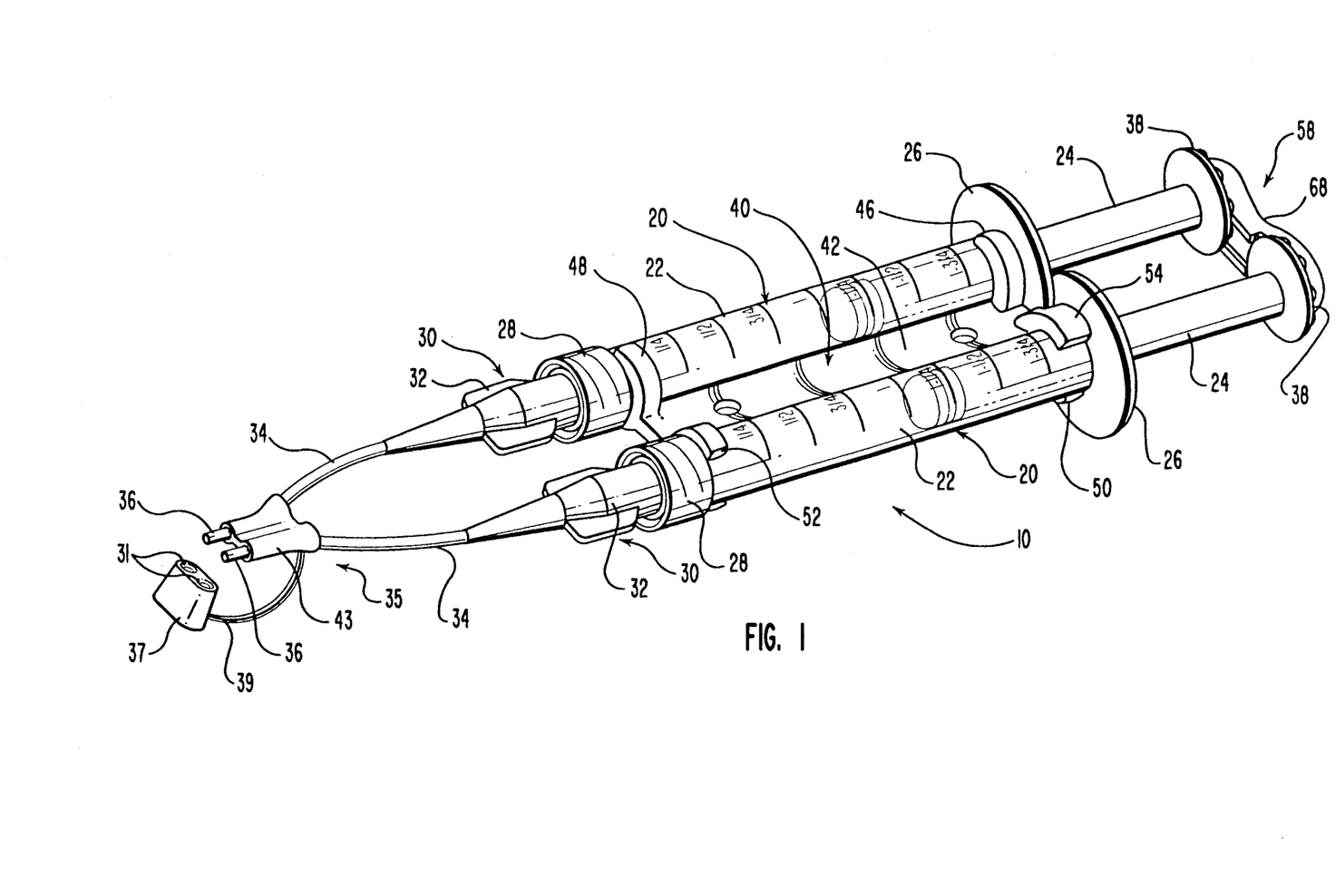
FIG. 1 is a perspective view of one presently preferred embodiment of the double syringe delivery system of the present invention.
Figure 2:
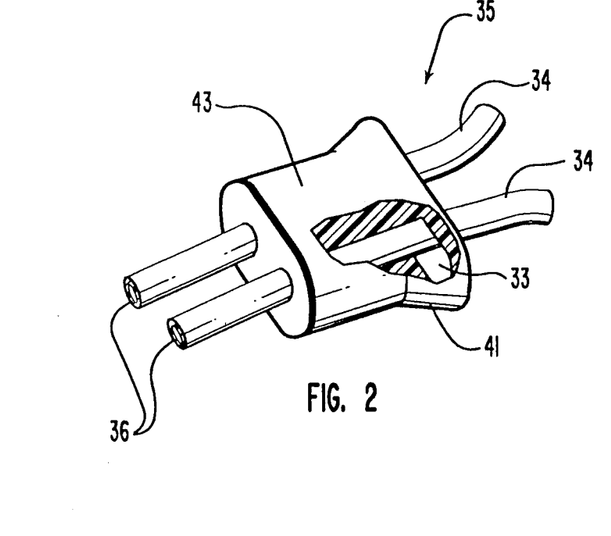
FIG. 2 is a perspective view of a retainer block that has been broken away to show two flexible delivery tubes inserted therein.
Figure 3:
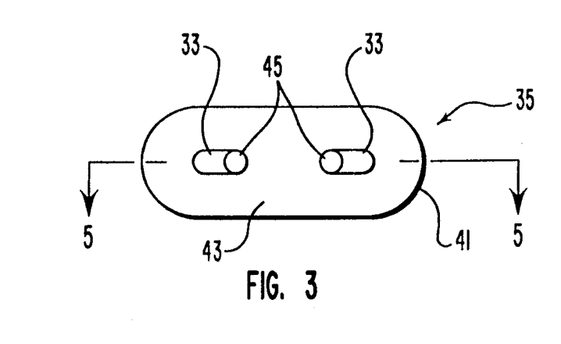
FIG. 3 is a top plan view of the retainer block.
Figure 4:
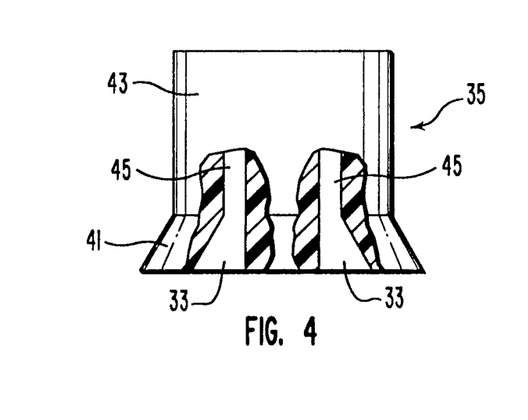
FIG. 4 is a side plan view of the retainer block broken away to show the lumen passages therethrough.
Figure 5:
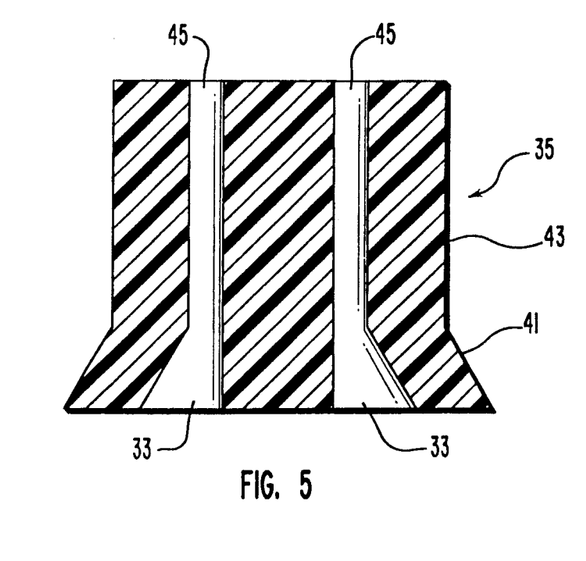
FIG. 5 is a cross sectional view of the retainer block taken along the 5—5 line of FIG. 3.

Reference is next made to the drawings wherein like parts are designated with like numerals throughout. Reference is first made to FIG. 1, which illustrates an enlarged perspective view of a double syringe delivery system in accordance with present invention, as generally indicated at reference numeral 10. The double syringe delivery system is used for holding a pair of standard syringes in a manner so as to accommodate simultaneous activation of the plunger of each syringe in order to effect simultaneous delivery of the contents of each syringe barrel. Accordingly, for purposes of illustrating the manner in which the double syringe delivery system can be used to that effect, two standard syringes are generally designated at 20. Each syringe 20 has a syringe barrel 22 from which fluid is to be dispensed. A syringe plunger 24 is inserted into the end of the syringe plunger 22 in standard fashion so that as the syringe plunger 24 is pushed into the barrel 22, the fluid contents of the barrel 22 are dispensed.

Each syringe 20 has a standard luer connector 28 at the delivery end of the barrel 22. In the illustrated embodiment, the luer connectors 28 are standard threaded female luer connectors. Attached at the delivery end of each syringe barrel 22 at the luer connectors 28 are delivery tips generally designated at 30. Each delivery tip 30 is comprised of a hub 32 which has a corresponding male luer connector for barrel 22. Attached to the hub 32 of each delivery tip is an elongated, tapered flexible delivery tube 34 through which the fluid contents of each syringe 20 is dispensed as will be hereinafter more fully described.

The other end of each syringe barrel 22 is equipped with a circular support disc 26 which provides a surface against which the fingers of a user can be pushed when exerting pressure on the plunger 24. The proximal end of plunger 24 has a circular push flange 38 so that by pushing on the flange 38 while at the same time pressing with the fingers on support disc 26, the syringe plunger 24 can be pushed into the syringe barrel 22 in a standard fashion. This, in turn, will effect delivery of the fluid contents of the syringe barrel 22 at the distal end 36 of each flexible, elongated delivery tube 34.

Figure 9:
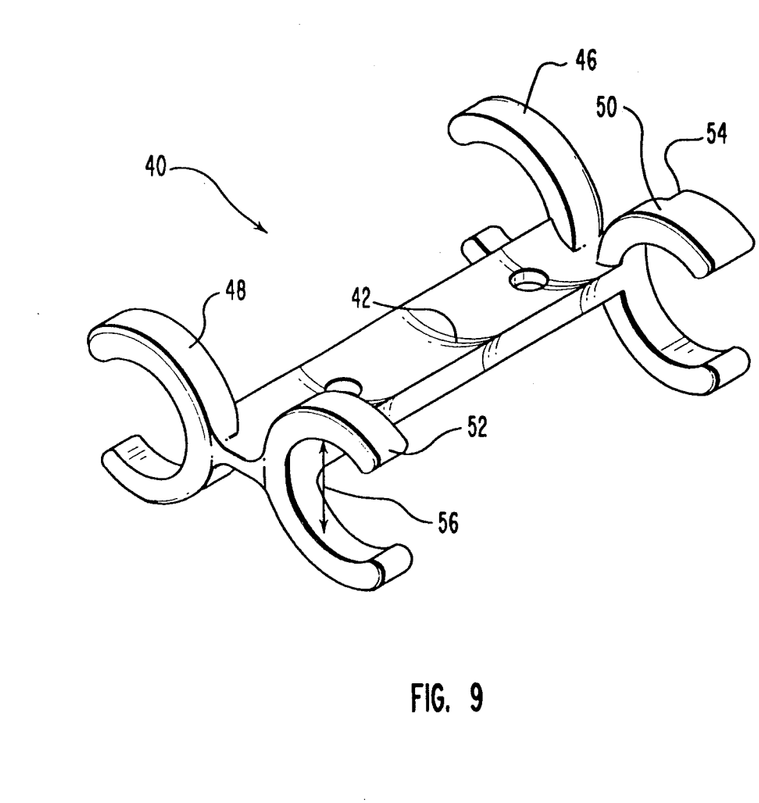
FIG. 9 is a perspective view of the clip assembly shown in FIG. 1.
Figure 10:
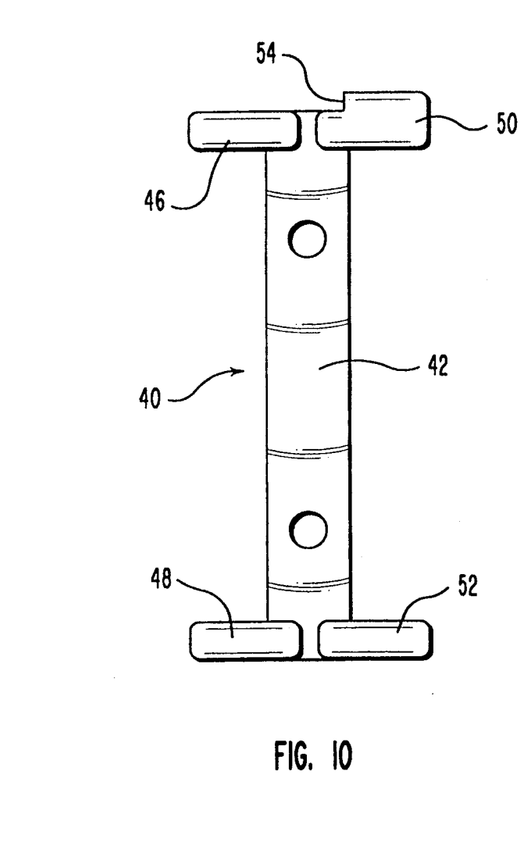
FIG. 10 is a front elevational view of the clip assembly.

In one aspect of the present invention, the double syringe delivery system is comprised of a first locking means for locking the syringe barrels 22 together in a parallel relationship wherein the barrels 22 are as close together as possible, but are still parallel, and wherein the barrels 22 are also locked in a manner so that they are slightly longitudinally offset from one another. By way of example and illustration in the drawings, and in particular with reference to FIGS. 1, 9, and 10 taken together, the first locking means is comprised of a clip assembly generally designated at 40, which has an elongated, generally flat support member 42 that is interposed between the two syringe barrels 22 so as to space them from one another in a parallel fashion.

In a further aspect of the invention, the first locking means is further comprised of a first collar means on one side of the support member 42 for attachment to the syringe barrel 22 of one of the syringes 20. A second collar means is similarly formed on an opposite side of the elongated support member 42 for attachment to the other syringe 20. Again, by way of example and illustration, each of the first and second collar means are comprised of two resilient C-shaped clamps that can be removably snapped onto a syringe barrel 22 for purposes of securely holding the syringes 20 in the manner described. As shown best in FIGS. 1 and 9, the elongated support member 42 has C-shaped clamps 46 and 48 formed on one side of the support member 42 and C-shaped clamps 50 and 52 formed on the opposite side of the support member 42. The width of each clamp 46, 48, 50, and 52, as schematically indicated at 56, is large enough so that each of the clamps can be snapped onto the cylindrical syringe barrel 22. As will be further appreciated from FIGS. 1, 9, and 10, the entire clip assembly generally designated at 40 is preferably constructed as a unitary, molded plastic piece which has sufficient resilience or memory so that the clip assembly can be snapped onto and off of standard syringes, thus permitting interchangeability of the syringes 20 as to either side of the clip assembly 40.

As further illustrated in FIG. 1, the clip assembly 40 is designed to hold the two syringes 20 parallel to one another, but at the same time as close together as possible. In this respect, it is to be noted that the two syringes 20 will be slightly longitudinally offset because they are held so closely together. In other words, the support discs 26 of the two syringes 20 will slightly overlap one another in order to permit the two syringes 20 to be held together as closely as possible. Because the two syringes 20 are longitudinally offset from one another by the width of one of the discs 26, the invention also preferably includes a spacer means for longitudinally offsetting one syringe from the other to permit or accommodate the overlapping relationship of the discs 26. As shown best in FIGS. 9 and 10, by way of illustration and example, the spacer means is comprised of a shoulder 54 which is formed on the C-shaped clamp 50. This shoulder 54 thus holds the support disc 26 of one of the syringes 20 in a manner so that it can overlap the other support disc 26.

As will be further noted in reference particularly to FIG. 1, the resilient C-shaped clamps which are formed on the opposite sides of elongated member 42 are longitudinally spaced from one another by a distance such that the clamps 46 and 50 will abut the support discs 26 of each syringe barrel 22, whereas the C-shaped clamps 48 and 52 will abut the luer connectors 28 at the opposite ends of the syringe barrels 22. In this fashion, the C-shaped clamps 46 and 48 as well as the C-shaped clamps 50 and 52 on the other side of the elongated support member 42 serve to lock the syringe barrels against any longitudinal movement relative to one another or relative to the elongated support member 42. Thus, not only are the syringes 20 held parallel to one another, but they are also locked into a slightly offset longitudinal relationship. This is advantageous because it permits the overall syringe delivery system to have a small width which therefore permits the delivery system to be more easily held and actuated when expelling fluid and pushing on the plungers 24.

In still a further aspect of the syringe delivery system of the present invention, the system is further comprised of a second locking means for locking the plungers 24 together in a parallel relationship and wherein the plungers 24 are also locked in the manner so that they are longitudinally offset by an amount that is the same as the longitudinal offset of the syringe barrels 22. By way of example and illustration, with particular reference to FIGS. 1 and 6-8 taken together, the second locking means is comprised of an assembly generally designated at 58. The second looking means is comprised of a are adapted for insertion into the hollow interior portion 25 of each syringe plunger 24. The first and second post 60 and 62 are in turn connected by an interconnecting bridge member 64 which joins the two together. In the preferred embodiment, the interconnecting bridge member 64 and the posts 60 and 62 are all formed as a unitary, molded plastic piece.

Figure 6:
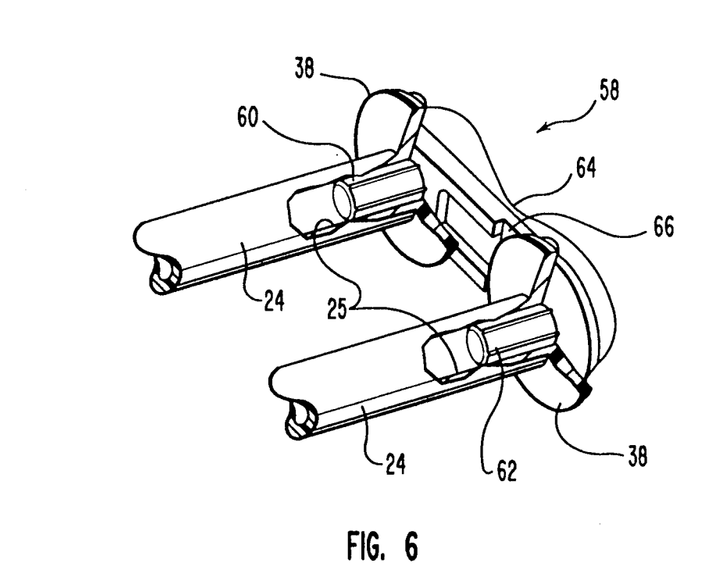
FIG. 6 is a perspective view with portions broken away to show a plunger cap, engaged with dual plungers, and showing dual plunger cap stems or extensions respectively inserted in the plungers.
Figure 7:
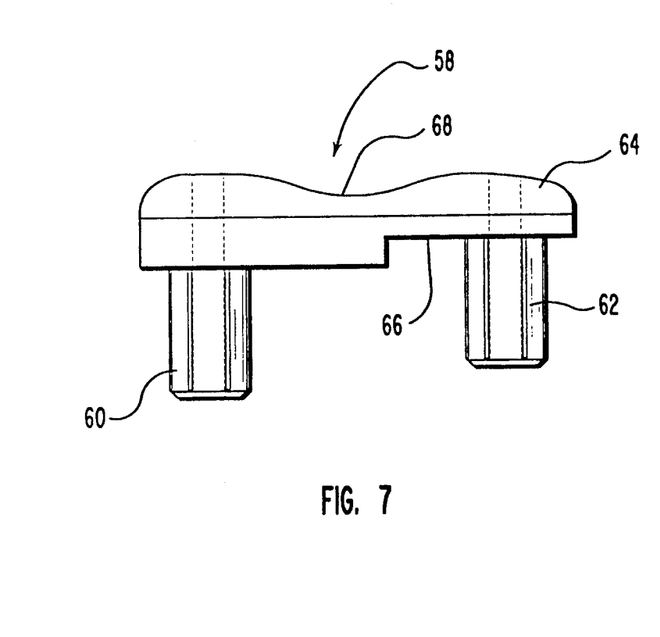
FIG. 7 is a front elevational plan view of the plunger cap.
Figure 8:
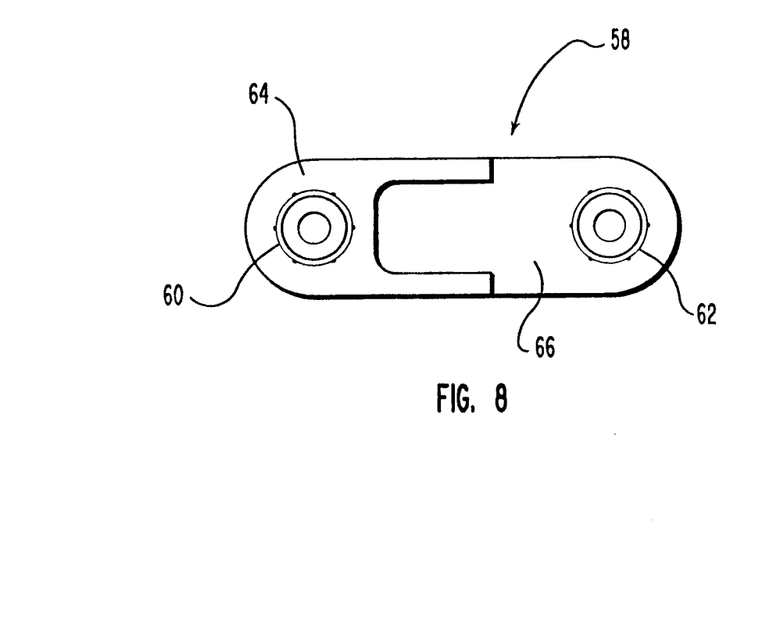
FIG. 8 is a bottom plan view of the plunger cap of FIG. 7.

As further illustrated in the drawings, at one end of the interconnecting bridge member 64 there is a notch 66. The notch 66 has a depth which is the same as the height of the shoulder 54. Accordingly this permits the push flanges 38 of the syringe plungers 24 to be longitudinally offset in an amount which is the same as the longitudinal offset that is created between the two syringe barrels 22 due to the overlapping discs 26. Accordingly, the interconnecting bridge member 68 will ensure that the two syringe plungers 24, even though slightly longitudinally offset with respect to each other, will simultaneously express the same amount of fluid irrespective of the longitudinal offset of the two plungers 24. The interconnecting bridge member 64 is also provided with a depression 68 which forms a comfortable location for a thumb or the palm of a hand when actuating the two plungers 24.

As further illustrated in the drawings, with particular reference to FIGS. 1-5 taken together, the double syringe delivery system of the present invention can also optionally comprise a retainer means for joining the flexible delivery tubes 34 together at their distal ends 36, as well as a cap means tethered to the retainer means for selectively capping the distal ends 36 of the delivery tubes 34. Again, by way of illustration and example in the drawings, the retainer means is illustrated as comprising a retainer block 43 that has passageways 45 formed therethrough for receiving the distal ends 36 of each flexible delivery tube 34. At the proximal end of the retainer block 43, the retainer block is flared as illustrated at 41 (see FIGS. 4 and 5) and the internal passageways 45 are similarly provided with flared openings 43 to permit easier access and entry of the delivery tubes 34 into the passageways 45. Since the retainer block 43 only secures the extreme distal ends 36 of the flexible delivery tubes 34, the flexible delivery tubes 34 are otherwise permitted to be bendable for ease in accessing any desired type of receptacle which is intended to receive the two fluids which are to be mixed.

The tethered cap means is illustrated in the drawings as comprising strap or tether 39 which is joined to the retainer block 43 at one end and which is joined at the other end to a removable cap 37 having two openings 31 which fit over the distal ends 36 of the delivery tubes 34. In the preferred embodiment, cap 37, strap or tether 39 and retainer block 43 are all preferably molded as a single unitary piece.

In a preferred method of using the double syringe delivery system of the present invention, two standard syringes 20 are first obtained and the delivery tips 30 are attached at the delivery ends of each syringe barrel 22. Each syringe barrel 22 is snapped into the two resilient, C-shaped clamps 46 and 48, and also 50 and 52 on opposite sides of the elongated support member 42. This secures the two syringes 20 in a parallel relationship, holding them as close together as possible so that the support discs 26 of the two syringes 20 are slightly overlapping each other.

Next, the retainer block 43 is slipped onto the distal ends 36 of the delivery tubes 34 and the cap 37 is placed over the distal ends 36 of each delivery tube 34. Lastly, the interconnecting bridge member 64 is secured to the proximal ends of each syringe plunger 24 by placing the post 60 into the hollow interior 25 of one of the syringe plungers 24 and placing the post 62 into the hollow interior 25 of the other syringe plunger 24. The cap 37 can then be removed and the syringe plungers 24 can be simultaneously activated by pushing against the interconnecting bridge member 64 in order to simultaneously express equal amounts, either drop-wise or faster, the fluid contents of each syringe 20, which can thereafter be mixed.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by U.S. Pat. No. is:

1. In a double syringe system wherein each syringe is comprised of a syringe barrel, a plunger and a delivery tip having an elongated, flexible delivery tube, a syringe delivery system for holding the syringes in a manner so as to accommodate simultaneous activation of the plunger of each syringe in order to effect simultaneous delivery of the contents of each syringe barrel, the delivery system comprising:

first locking means for locking the syringe barrels together in a parallel relationship wherein the barrels are as close together as possible, but are still parallel, and wherein the barrels are also locked in a manner so that they are slightly longitudinally offset from one another; and second locking means for locking the plungers together in a parallel relationship and wherein the plungers are also locked in a manner so that they are longitudinally offset by an amount that is the same as the longitudinal offset of the syringe barrels.

2. A syringe delivery system as defined in claim 1, wherein each syringe is further comprised of a luer connector for attaching the delivery tip at one end of the syringe barrel, and a support disc at the other end of the syringe barrel, and wherein the first locking means comprises:

an elongated support member interposed between the syringe barrels so as to space them from one another;

first collar means on one side of the support member for attachment of the support member to one syringe at the luer connector and at the support disc of said one syringe so as to prevent axial movement of the one syringe relative to the support member; and second collar means on an opposite side of the support member for attachment of the support member to the other syringe at the luer connector and at the support disc of said other syringe so as to prevent axial movement of the other syringe relative to the support member.

3. A syringe delivery system as defined in claim 2, wherein the support member has a width sized so as to space the syringes as close as possible, such that the disc of one syringe overlaps the disc of the other syringe.

4. A syringe delivery system as defined in claim 3, wherein one of the first and second collar means comprises spacer means for longitudinally offsetting one syringe from another so as to permit the overlapping relationship of the syringe discs.

5. A syringe delivery system as defined in claim 2, wherein each said collar means comprises a first resilient C-shaped clamp that can be removeably snapped onto a syringe barrel so as to abut the disc of the syringe barrel, and a second C-shaped clamp that can be removably snapped onto a syringe barrel and longitudinally spaced from the first clamp so as to abut the luer connector of the syringe barrel when snapped into place.

6. A syringe delivery system as defined in claim 4, wherein the elongated support member, first and second collar means and the spacer means are all formed as a single, unitary piece.

7. A syringe delivery system as defined in claim 1, wherein each syringe plunger has a push flange at a proximal end thereof, and wherein the second locking means is seated on the push flange of each syringe plunger and comprises means for joining the push flange of one plunger to the push flange of the other plunger.

8. A syringe delivery system as defined in claim 1, wherein each plunger is a cylindrical member with a hollow interior, and wherein the second locking means comprises:

a first post adapted for insertion into the interior of one plunger;

a second post adapted for insertion into the interior of the other plunger; and an interconnecting bridge member joined to the two posts.

9. A syringe delivery system as defined in claim 8, wherein the bridge member is notched on one side thereof so as to accommodate the amount by which the plungers are vertically offset.

10. A syringe delivery system as defined in claim 1, further comprising retainer means for joining the flexible delivery tubes together at their distal ends.

11. A syringe delivery system as defined in claim 10 further comprising cap means tethered to the retainer means for selectively capping the distal ends of the delivery tubes.

12. In a double syringe system wherein each syringe is comprised of a syringe barrel having a luer connector at one end thereof and a support disc at the other end thereof, a plunger slidably situated in the syringe barrel and a delivery tip attached at the luer connector and having an elongated flexible delivery tube, a syringe delivery system for holding the syringes in a manner so as to accommodate simultaneous activation of the plunger of each syringe in order to effect simultaneous delivery of the contents of each syringe barrel, the delivery system comprising:

an elongated support member interposed between the syringe barrels so as to space them from one another;

first collar means on one side of the support member for attachment of the support member to one syringe at the luer connector and at the support disc of said one syringe so as to prevent axial movement of the one syringe relative to the support member;

second collar means on an opposite side of the support member for attachment of the support member to the other syringe at the luer connector and at the support disc of said other syringe so as to prevent axial movement of the other syringe relative to the support member, and wherein one of said first and second collar means comprise spacer means for longitudinally offsetting the syringes from one another so as to permit the discs at the ends of each syringe barrel to overlap one another, thereby locking the syringe barrels together in a parallel relationship wherein the barrels are as close together as possible; and interconnecting bridge means for locking the plungers together in a parallel relationship and wherein the plungers are also locked in a manner so that they are longitudinally offset by an amount that is the same as the longitudinal offset of the syringe barrels.

13. A syringe delivery system as defined in claim 12, wherein the elongated support member, first and second collar means and the spacer means are all formed as a single, unitary piece.

14. A syringe delivery system as defined in claim 13, wherein each said collar means comprises a first resilient C-shaped clamp that can be removeably snapped onto a syringe barrel so as to abut the support disc of the syringe barrel, and a second C-shaped clamp that can be removably snapped onto the same syringe barrel and longitudinally spaced from the first clamp so as to abut the luer connector of the syringe barrel when snapped into place.

15. A syringe delivery system as defined in claim 14, wherein each syringe plunger has a push flange at a proximal end thereof, and wherein the second locking means is seated on the push flange of each syringe plunger and comprises means for joining the push flange of one plunger to the push flange of the other plunger.

16. A syringe delivery system as defined in claim 14, wherein each plunger is a cylindrical member with a hollow interior, and wherein the second locking means comprises:
   a first post adapted for insertion into the interior of one plunger;
   a second post adapted for insertion into the interior of the other plunger; and
   an interconnecting bridge member joined to the two posts.

17. A syringe delivery system as defined in claim 16, wherein the bridge member is notched on one side thereof so as to accommodate the amount by which the plungers are vertically offset.

18. A syringe delivery system as defined in claims 15 or 16 further comprising means for joining the flexible delivery tubes together at their distal ends.

19. A syringe delivery system as defined in claim 18 further comprising cap means tethered to the retainer means for selectively capping the distal ends of the delivery tubes.

20. In a double syringe system wherein each syringe is comprised of a syringe barrel having a luer connector at one end thereof and a support disc at the other end thereof, a hollow cylindrical plunger slidably situated in the syringe barrel and a delivery tip attached at the luer connector and having an elongated flexible delivery tube, a syringe delivery system for holding the syringes in a manner so as to accommodate simultaneous activation of the plunger of each syringe in order to effect simultaneous delivery of the contents of each syringe barrel, the delivery system comprising:

an elongated support member interposed between the syringe barrels so as to space them from one another;

first collar means on one side of the support member for attachment of the support member to one syringe at the luer connector and at the support disc of said one syringe so as to prevent axial movement of the one syringe relative to the support member;

second collar means on an opposite side of the support member for attachment of the support member to the other syringe at the luer connector and at the support disc of said other syringe so as to prevent axial movement of the other syringe relative to the support member, and wherein one of said first and second collar means comprise spacer means for longitudinally offsetting the syringes from one another so as to permit the discs at the ends of syringe barrel to overlap one another, thereby locking the syringe barrels together in a parallel relationship wherein the barrels are as close together as possible, and wherein each said collar means comprises a first resilient C-shaped clamp that can be removeably snapped onto a syringe barrel so as to abut the support disc of the syringe barrel, and a second C-shaped clamp that can be removably snapped onto the same syringe barrel and longitudinally spaced from the first clamp so as to abut the luer connector of the syringe barrel when snapped into place;

interconnecting bridge means for locking the plungers together in a parallel relationship and wherein the plungers are also locked in a manner so that they are longitudinally offset by an amount that is the same as the longitudinal offset of the syringe barrels, and wherein the second locking means comprises:
   a first post adapted for insertion into the hollow of one plunger;
   a second post adapted for insertion into the hollow of the other plunger;
   an interconnecting bridge member joined to the two posts, and wherein the bridge member is notched on one side thereof so as to accommodate the amount by which the plungers are vertically offset;

retainer means for joining the flexible delivery tubes together at their distal ends; and further comprising cap means tethered to the retainer means for selectively capping the distal ends of the delivery tubes.

* * * * *

UNITED STATES PATENT AND TRADEMARK OFFICE
CERTIFICATE OF CORRECTION

PATENT NO.   :   5,290,259
DATED        :   March 1, 1994
INVENTOR(S)  :   DAN E. FISCHER It is certified that error appears in the above-indentified patent and that said Letters Patent is hereby corrected as shown below:

Column 2, line 63, before "Elongated" insert --The--
Column 3, line 58, after "with" insert --the--
Column 5, line 52, after "of a" insert --first post 60 and a second post 62 (See Figures 6 and 7) which--
Column 5, line 51, "looking" should be --locking--

Signed and Sealed this

Eighth Day of November, 1994

Attest:

BRUCE LEHMAN

Attesting Officer        Commissioner of Patents and Trademarks